United States Patent [19]

Woods

[11] Patent Number: 5,501,652

[45] Date of Patent: Mar. 26, 1996

[54] SELF-EXAMINATION OTOSCOPE

[76] Inventor: William A. Woods, 3009 Kings La., Nashville, Tenn. 37218

[21] Appl. No.: 306,420

[22] Filed: Sep. 15, 1994

[51] Int. Cl.⁶ .................................................. A61B 1/227
[52] U.S. Cl. .......................... 600/200; 600/245; 600/248; 600/249
[58] Field of Search ...................... 128/3, 5, 7, 9, 128/11, 22; 606/13–19; 359/402, 405, 406; 600/200, 245, 248, 249

[56] References Cited

U.S. PATENT DOCUMENTS

| | | | |
|---|---|---|---|
| 1,896,861 | 2/1933 | Cameron | 600/200 |
| 1,990,972 | 2/1935 | Arnesen | 600/200 |
| 2,823,666 | 2/1958 | Hallpike et al. | 600/200 |
| 3,874,371 | 4/1975 | Stader et al. | 600/200 |

FOREIGN PATENT DOCUMENTS

000012817A1  7/1980  European Pat. Off. ............ 600/248

*Primary Examiner*—Richard J. Apley
*Assistant Examiner*—Kelly McGlashen

[57] ABSTRACT

A self-examination otoscope for allowing a user to examine an eardrum and external canal of one of his own ears comprising an elongated bored housing having an eyepiece end positionable near a user's eye for viewing and a speculum end simultaneously positionable within the user's ear; a lamp mechanism coupled to the housing for transmitting light towards the user's ear when the speculum end of the housing is positioned therein; a power source mechanism for supplying electrical energy to the lamp mechanism; a light direction mechanism secured within the housing for directing light entering the speculum end towards the eyepiece end; and a lens mechanism secured within the housing for allowing light transmitted towards the eyepiece end to be focused for allowing the user a clear view of his ear.

4 Claims, 4 Drawing Sheets

SELF-EXAMINATION OTOSCOPE

BACKGROUND OF THE INVENTION

1. Field of the Invention

The present invention relates to a self-examination otoscope and more particularly pertains to allowing a user to examine an eardrum and external canal of one of his own ears with a self-examination otoscope.

2. Description of the Prior Art

The use of otoscopes is known in the prior art. More specifically, otoscopes heretofore devised and utilized for the purpose of examining an ear are known to consist basically of familiar, expected and obvious structural configurations, notwithstanding the myriad of designs encompassed by the crowded prior art which have been developed for the fulfillment of countless objectives and requirements.

By way of example, U.S. Pat. No. Des. 336,133 to Burgio et al. discloses an otoscope. U.S. Pat. No. 3,874,371 to Stader et al. discloses an otoscope. U.S. Pat. No. 4,335,713 to Komiya discloses an otoscope. U.S. Pat. No. 4,685,452 to Riester discloses an otoscope with pivotally mounted loupe. U.S. Pat. No. 4,925,285 to Dowdell et al. discloses an apparatus to permit anatomical self examination.

While these devices fulfill their respective, particular objective and requirements, the aforementioned patents do not describe an otoscope that allows a user to perform a self-examination of his ears.

In this respect, the self-examination otoscope according to the present invention substantially departs from the conventional concepts and designs of the prior art, and in doing so provides an apparatus primarily developed for the purpose of allowing a user to examine an eardrum and external canal of one of his own ears.

Therefore, it can be appreciated that there exists a continuing need for new and improved self-examination otoscope which can be used for allowing a user to examine an eardrum and external canal of one of his own ears. In this regard, the present invention substantially fulfills this need.

SUMMARY OF THE INVENTION

In the view of the foregoing disadvantages inherent in the known types of otoscopes now present in the prior art, the present invention provides an improved self-examination otoscope. As such, the general purpose of the present invention, which will be described subsequently in greater detail, is to provide a new and improved self-examination otoscope and method which has all the advantages of the prior art and none of the disadvantages.

To attain this, the present invention essentially comprises, in combination, an eyepiece component. The eyepiece component includes a hollow rigid elbow having a circular cross-section, an open eyepiece end, an open base end, and a perpendicular bend therebetween. The eyepiece component includes an adjustable magnifying lens coupled to the eyepiece end. Lastly, the eyepiece component includes a mirror disposed therein and secured at the bend in a position for directing light entering the base end towards the eyepiece end.

A speculum component is provided. The speculum component includes a hollow rigid elbow having a circular cross-section, a conical open speculum end, an open base end having a diameter greater than the speculum end, and a perpendicular bend therebetween. The speculum component includes a removable door formed thereon between the bend and base end. The speculum component includes a mirror disposed within the elbow and secured at the bend in a position for directing light entering the speculum end towards the base end. The speculum component includes a lamp disposed within the elbow and secured thereto at a location between the speculum end and bend for directing light through the speculum end when electrically energized. The speculum component includes a battery disposed within the elbow and secured thereto at a location adjacent to the door for supplying electrical energy. Lastly, the speculum component includes a power switch coupled between the lamp and battery and extended through the elbow near the bend with the power switch having an enabled orientation for allowing the lamp to be electrically energized and a disabled orientation for preventing the lamp from being electrically energized.

Lastly, a central component is provided. The central component includes a hollow rigid elbow having a circular cross-section, an open first end removably and telescopically mated with the base end of the speculum component, an open second end removably and telescopically mated with the base end of the eyepiece component, and a perpendicular bend therebetween. The speculum component also includes a mirror disposed within the elbow and secured at the bend in a position for directing light entering the first end towards the second end. When the speculum end is disposed within a user's ear, the eyepiece end is positioned near a user's eye for viewing, and the power switch is placed in the enabled orientation, light transmitted from the lamp is reflected from an ear drum and external canal of the user's ear and transmitted through the elbows and through the magnifying lens, thus allowing the user to perform a self-examination of his own ear.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved self-examination otoscope which has all the advantages of the prior art otoscopes and none of the disadvantages.

It is another object of the present invention to provide a new and improved self-examination otoscope which may be easily and efficiently manufactured and marketed.

It is a further object of the present invention to provide a new and improved self-examination otoscope which is of durable and reliable construction.

An even further object of the present invention is to provide a new and improved self-examination otoscope which is susceptible of a low cost of manufacture with regard to both materials and labor, and which accordingly is then susceptible of low prices of sale to the consuming public, thereby making such a self-examination otoscope economically available to the buying public.

Still yet another object of the present invention is to provide a new and improved self-examination otoscope which provides in the apparatuses and methods of the prior art some of the advantages thereof, while simultaneously overcoming some of the disadvantages normally associated therewith.

Even still another object of the present invention is to provide a new and improved self-examination otoscope for allowing a user to examine an eardrum and external canal of one of his own ears.

Lastly, it is an object of the present invention to provide a new and improved self-examination otoscope comprising an elongated bored housing having an eyepiece end positionable near a user's eye for viewing and a speculum end simultaneously positionable within the user's ear; lamp means coupled to the housing for transmitting light towards the user's ear when the speculum end of the housing is positioned therein; power source means for supplying electrical energy to the lamp means; light direction means secured within the housing for directing light entering the speculum end towards the eyepiece end; and lens means secured within the housing for allowing light transmitted towards the eyepiece end to be focused for allowing the user a clear view of his ear.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various figures.

DESCRIPTION OF THE PREFERRED EMBODIMENT

Figure 1:
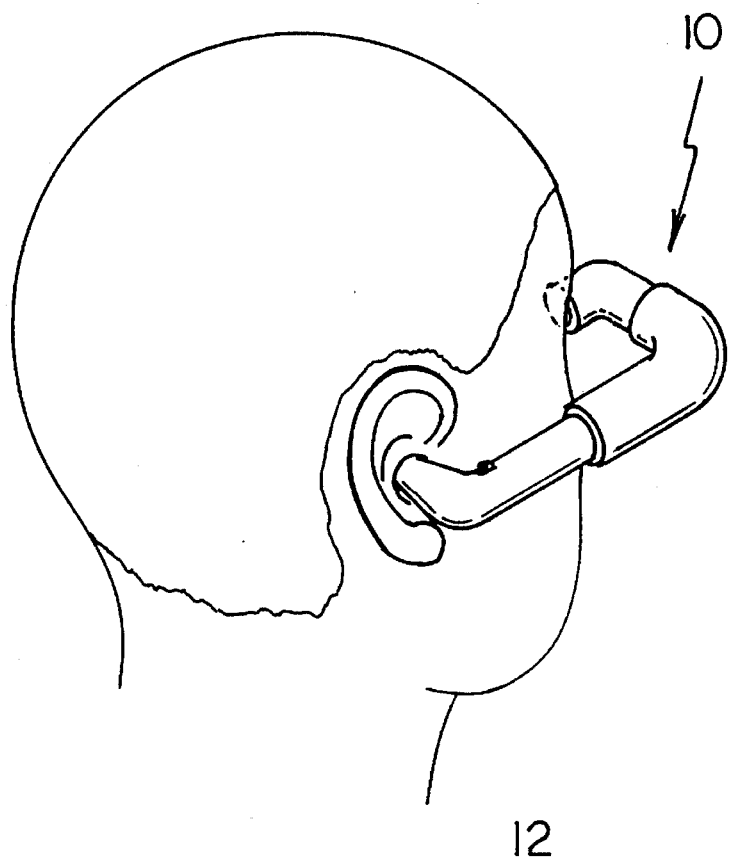
FIG. 1 is a perspective view of the preferred embodiment constructed in accordance with the principles of the present invention positioned upon a user's head for permitting self-examination of his ear.
Figure 2:
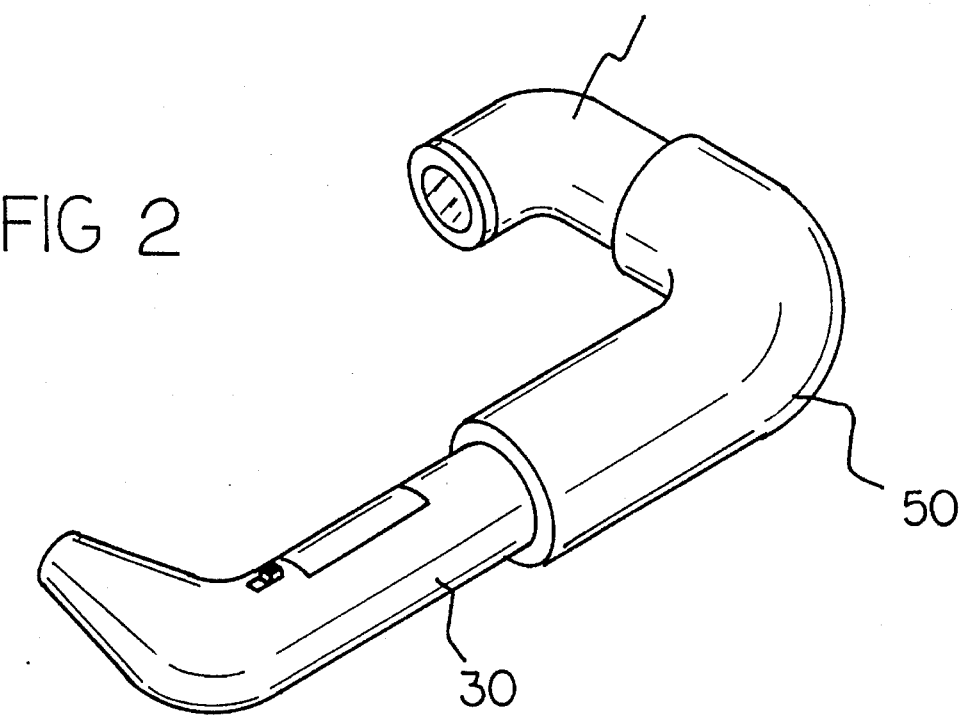
FIG. 2 is a perspective view of the preferred embodiment constructed in accordance with the principles of the present invention.
Figure 3:
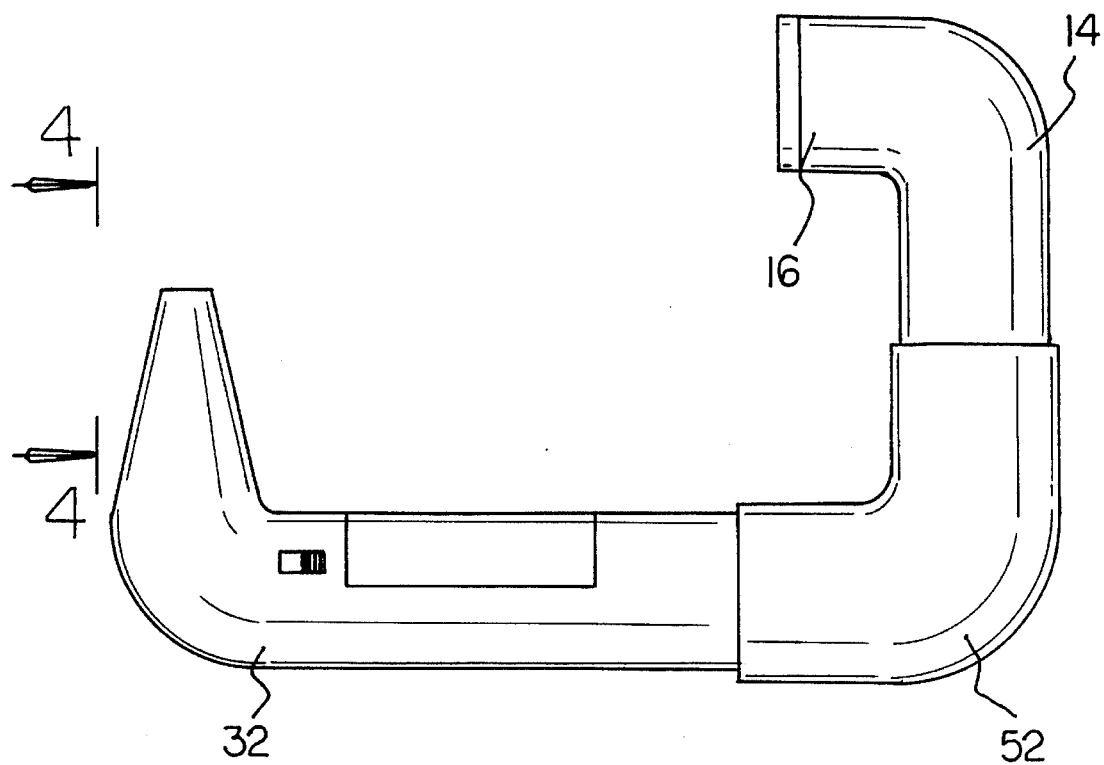
FIG. 3 is a plan view of the present invention.
Figure 4:
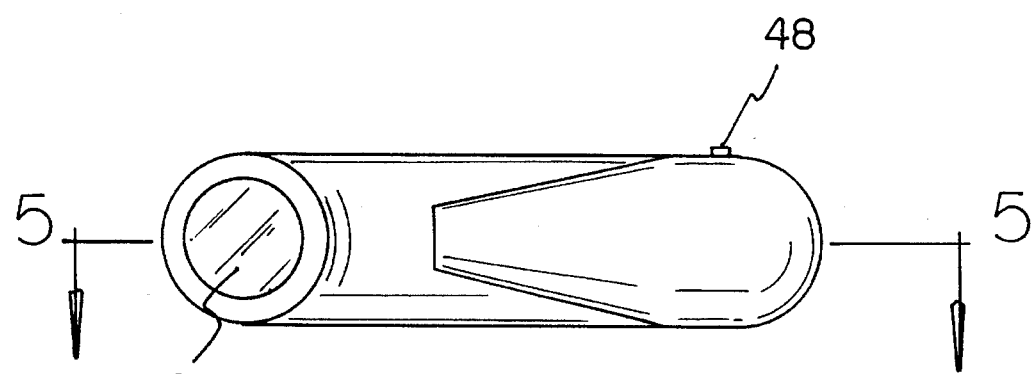
FIG. 4 is a side elevational view of the present invention taken along the line 4—4 of FIG. 3.
Figure 5:
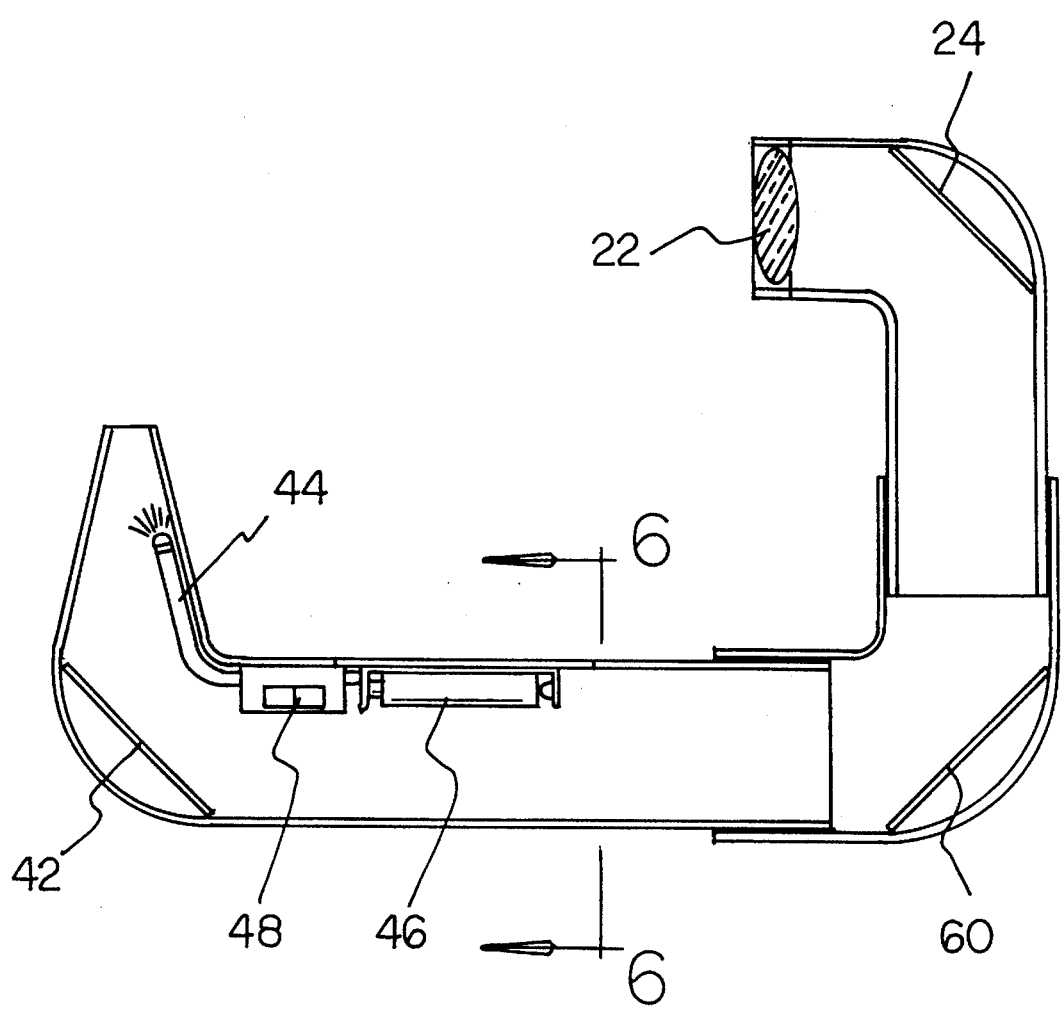
FIG. 5 is a cross-sectional view of the present invention taken along the line 5—5 of the FIG. 4.
Figure 6:
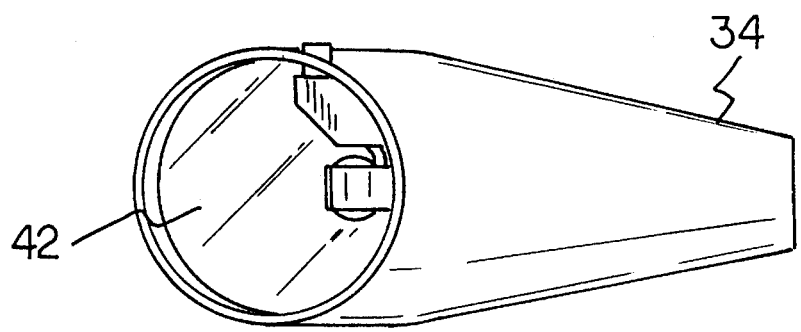
FIG. 6 is a cross-sectional view of the third elbow taken along the line 6—6 of FIG. 5.
Figure 7:
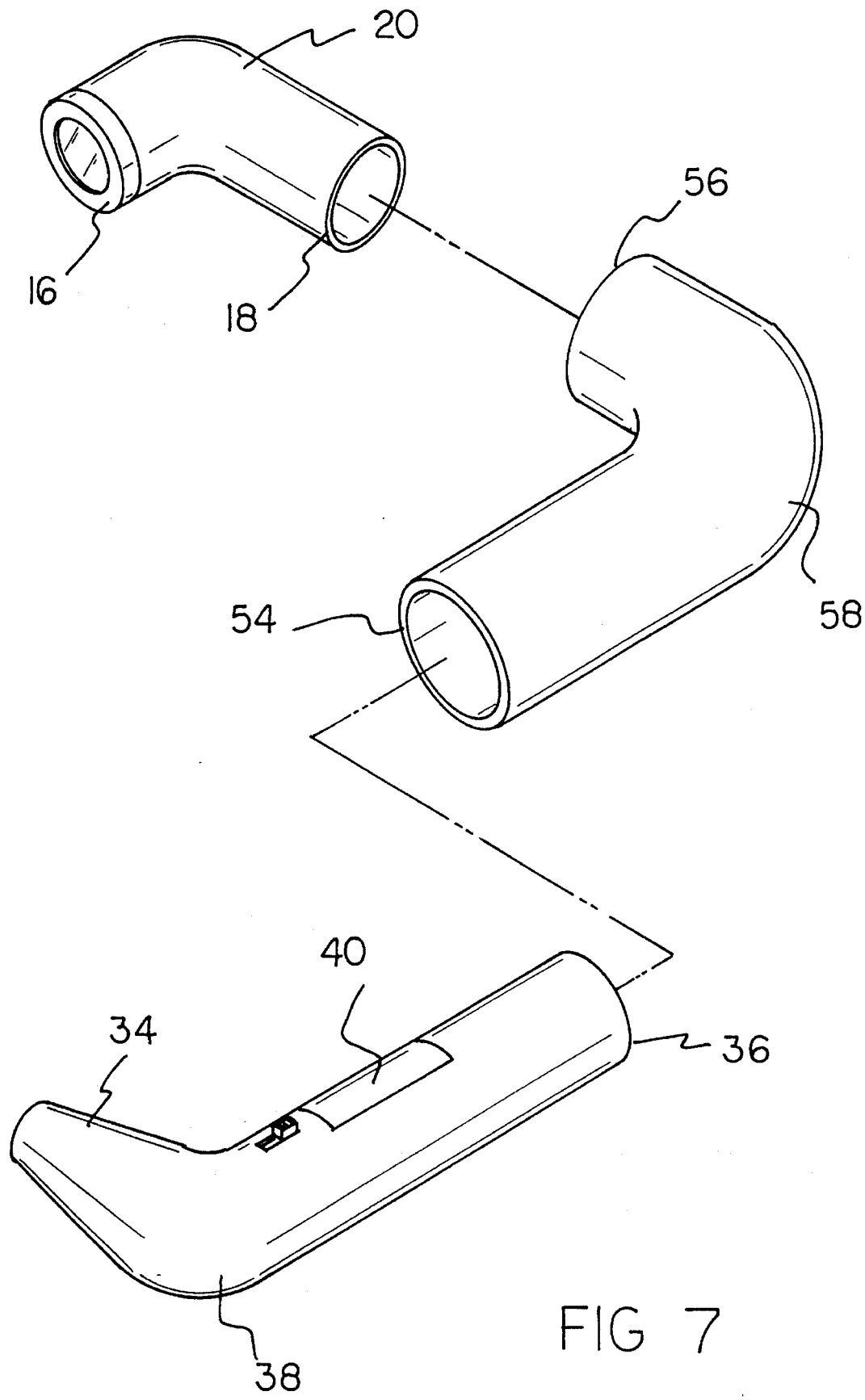
FIG. 7 is an exploded perspective view of the present invention.

With reference now to the drawings, and in particular, to FIG. 1 thereof, the preferred embodiment of the new and improved self-examination otoscope embodying the principles and concepts of the present invention and generally designated by the reference number 10 will be described.

Specifically, the present invention essentially includes three major components. The major components are the eyepiece component, speculum component, and central component. These components are interrelated to provide the intended function of allowing a user to perform a self-examination of an eardrum and external canal of one of his ears.

More specifically, it will be noted in the various figures that the first major component is the eyepiece component 12. The eyepiece component essentially includes three subcomponents. The first subcomponent is the elbow 14. The elbow is hollow and rigid in structure. It is formed of plastic or other similar material. The elbow has a circular cross-section. The elbow further includes an open eyepiece end 16, and open base end 18, and a perpendicular bend 20 therebetween. The second subcomponent is the magnifying lens 22. The magnifying lens is coupled to the eyepiece end of the elbow. The magnifying lens is used to adjust focus of light passing through it. The lens is formed of glass or plastic. The third subcomponent is the mirror 24. The mirror is planar in structure. It is disposed within the elbow and secured at the bend. The mirror is used for directing light entering the base end towards the eyepiece end.

The second major component is the speculum component 30. The speculum component essentially includes six subcomponents. The first subcomponent is the elbow 32. The elbow is hollow and rigid in structure. It is formed of plastic or other similar material. The elbow has a circular cross section. The elbow further includes an open speculum end 34, an open base end 36 having a diameter greater than the speculum end, and a perpendicular bend 38 therebetween. The second subcomponent is the door 40. The door is formed between the bend and base end on the elbow. The door may be secured to the elbow in one orientation and removed therefrom in another orientation. The third subcomponent is the mirror 42. The mirror is planar in structure. It is disposed within the elbow and secured at the bend. The mirror is positioned for directing light entering the speculum end towards the base end 36. The fourth subcomponent is the lamp 44. The lamp is disposed within the elbow and secured thereto at a location between the speculum end and bend. The lamp is used for directing light through the speculum end when electrically energized for illuminating a user's ear. The fifth subcomponent is the battery 46. The battery is disposed within the elbow and secured thereto at a location adjacent to the door. The battery is used for supplying electrical energy to the lamp. The battery is conventional in design and commercially available. The sixth subcomponent is the power switch 48. The power switch is coupled between the lamp and battery. The power switch extends through the elbow to the exterior. The power switch has an enabled orientation for allowing the lamp to be electrically energized with electrical energy from the battery. The switch has another disabled orientation for preventing the lamp from being electrically energized by the battery.

The third major component is central component 50. The central component includes two subcomponents. The first subcomponent is the elbow 52. The elbow is hollow and rigid in structure. It is formed of plastic or other similar material. The elbow has a circular cross section. The elbow also has an open first end 54 removeably and telescopically mated with the base end 36 of the speculum component. In this configuration, the speculum component may be adjusted inwards or outwards with respect to the central component. The central component also has an open second end 56 removeably and telescopically mated with the base end of the eyepiece component 18. In this configuration, the eyepiece component may be adjusted inwards and outwards with respect to the central component. The elbow of the central component also includes a perpendicular bend 58 formed between the first end and second end. The second subcomponent is the mirror 60. The mirror is planar in structure. The mirror is positioned for directing light entering the first end towards the second end.

To operate the present invention, the speculum component and eyepiece component are secured to the central component. The speculum end is then disposed within a user's ear, and the eyepiece end is positioned near a user's eye. The power switch is then placed in the enabled orientation. Light transmitted from the lamp is reflected from an eardrum and external canal of the user's ear. This reflected light is transmitted through the speculum end and through the elbows to the magnifying lens. The magnifying lens may then be adjusted by a user to provide a clear view of his ear. Thus, a user may then perform a self-examination of his ear.

The present invention is a three bend optical device which enables a user to look into one of his own ears. The present invention performs the same function as an otoscope that doctors use to examine a patient's ear. The present invention utilizes a magnifying lens and a lamp powered by a battery. To perform a self-examination the opening into the ear canal is spread out by the conical speculum end of the speculum component to obtain a clear view. Light must travel through the present invention over a path with an angular extent of 270 degrees as measured radially from an ear located at the speculum end of the speculum component to an eye located at the eyepiece end of the eyepiece component. To allow the transmission of reflected light from a user's ear the present invention has a plastic elbow assembly which has three perpendicular bends. Mirrors are mounted within the elbows at the bends. Each mirror is inclined at 45 degrees relative to the perpendicular axes of an elbow. Adjoining elbows can be telescopically adjusted to change the length of the present invention to suit each user's head. The central component of the present invention has a diameter of approximately 3 inches. When the elbows are connected together and extended to their full length, the present invention as measured from the speculum end of the speculum component to the eyepiece of the eyepiece component along a common central axis defined when the elbows are connected is about 6 inches. A self-contained pen light or lamp illuminates a user's ear for conducting the self-examination. The pen light or lamp is powered by a battery. The battery may be removed through a door formed on the third elbow.

After the present invention is adjusted to fit a user's head, the lamp is turned on using the power switch. The magnifying lens near the eyepiece end of the eyepiece component is then adjusted to provide a clear view of a user's ear. The present invention is stored with the elbows separated, thus reducing its space envelope so it can easily fit into a drawer. After illnesses and infections, a user who lives alone can examine his ears to see if any damage has been inflicted. Use of the present invention is prescribed in accordance with instructions of a doctor who specializes in that area of medicine.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A self-examination otoscope for allowing a user to examine an eardrum and external canal of one of his own ears comprising, in combination:

an eyepiece component further comprising:
   a hollow rigid elbow having a circular cross-section, an open eyepiece end, an open base end, and a perpendicular bend therebetween;
   an adjustable magnifying lens coupled to the eyepiece end; and
   a mirror disposed therein and secured at the bend at a position for directing light entering the base end towards the eyepiece end;

a speculum component further comprising:
   a hollow rigid elbow wish an interior and exterior portion and further having a circular cross-section, a conical open speculum end, an open base end having a diameter greater than the speculum end, and a perpendicular bend therebetween;
   a removable door formed thereon between the bend and base end;
   a mirror disposed within the elbow and secured at the bend in a position for directing light entering the speculum end towards the base end;
   a lamp disposed within the elbow and secured thereto at a location between the speculum end and bend for directing light through the speculum end when electrically energized;
   a battery disposed within the elbow and secured thereto at a location adjacent to the door for supplying electrical energy; and a power switch coupled between the lamp and battery and extended through the elbow to the exterior thereof with the power switch having an enabled orientation for allowing the lamp to be electrically energized and a disabled orientation for preventing the lamp from being electrically energized; and a central component further comprising:

a hollow rigid elbow having a circular cross-section, an open first end removably and telescopically mated with the base end of the speculum component, an open second end removably and telescopically mated with the base end of the eyepiece component, and a perpendicular bend therebetween; and a mirror disposed within the elbow and secured at the bend in a position for directing light entering the first end towards the second end;

whereby when the speculum end is disposed within a user's ear, the eyepiece end is positioned near a user's eye for viewing, and the power switch is placed in the enabled orientation, light transmitted from the lamp is reflected from an ear drum and external canal of the user's ear and transmitted through the elbows and through the magnifying lens, thus allowing the user to perform a self-examination of his own ear.

2. A self-examination otoscope for allowing a user to examine an eardrum and external canal of one of his own ears comprising:

an elongated bored housing having an eyepiece end configured to be positionable near user's eye for viewing and a speculum end configured so as to be simultaneously positioned within the user's ear;

lamp means coupled to the housing for transmitting light towards the user's ear;

power source means for supplying electrical energy to the lamp means;

light direction means secured within the housing for directing light entering the speculum end towards the eyepiece end; and adjustable lens means secured within the housing for allowing light transmitted towards the eyepiece end to be focused into the eye of the user.

3. The self-examination otoscope as set forth in claim 2 wherein the housing is formed of a plurality of telescopically mated and adjustable segments coupleable in an end-to-end operable configuration and decoupleable in a stowed configuration.

4. The self-examination otoscope as set forth in claim 2 further including power switch means coupled between the lamp means and power source means and having an enabled origination for allowing the lamp means to be electrically energized and a disabled orientation for preventing the lamp means from being electrically energized.

* * * * *